(12) United States Patent
Hafenscher et al.

(10) Patent No.: US 7,671,244 B2
(45) Date of Patent: Mar. 2, 2010

(54) METHOD FOR PRODUCING 1,2-DICHLOROETHANE BY MEANS OF DIRECT CHLORINATION

(75) Inventors: Harald Hafenscher, Sulzbach (DE); Reinhold Weis, Kelkeim (DE); Michael Benje, Darmstadt (DE)

(73) Assignee: UHDE GmbH, Dortmund (DE)

( * ) Notice: Subject to any disclaimer, the term of this patent is extended or adjusted under 35 U.S.C. 154(b) by 0 days.

(21) Appl. No.: 11/793,882

(22) PCT Filed: Dec. 15, 2005

(86) PCT No.: PCT/EP2005/013535

§ 371 (c)(1),
(2), (4) Date: Oct. 11, 2007

(87) PCT Pub. No.: WO2006/069640

PCT Pub. Date: Jul. 6, 2006

(65) Prior Publication Data

US 2008/0146854 A1    Jun. 19, 2008

(30) Foreign Application Priority Data

Dec. 22, 2004 (DE) .................. 10 2004 063 090

(51) Int. Cl.
*C07C 17/02* (2006.01)
*C07C 17/093* (2006.01)

(52) U.S. Cl. .................. 570/247; 570/246; 570/252

(58) Field of Classification Search ............... 570/247, 570/246, 252

See application file for complete search history.

(56) References Cited

U.S. PATENT DOCUMENTS

| 3,594,428 A | * | 7/1971 | Antonini et al. ............. 570/222 |
| 6,841,708 B1 | | 1/2005 | Benje |
| 7,009,084 B2 | | 3/2006 | Benje et al. |

FOREIGN PATENT DOCUMENTS

| DE | 199 10 964 A1 | 9/2000 |
| WO | WO 03/070673 A1 | 8/2003 |

* cited by examiner

*Primary Examiner*—Jafar Parsa
(74) *Attorney, Agent, or Firm*—Marshall & Melhorn, LLC

(57) ABSTRACT

The invention relates to a method for producing high-purity 1,2-dichloroethane from dissolved chlorine and dissolved ethylene which are brought into contact with each other using a circulating liquid reaction medium which essentially consists of 1,2-dichloroethane and a catalyst and passes through at least one reaction loop. The two limbs of the loop are connected to a gas-phase stripping container which is arranged at the top and from which the reaction product is outwardly transferred either in a gaseous or liquid form or both in a gaseous form and in a liquid form. The addition points for the addition of chlorine and dissolved ethylene are arranged in the limb of the loop in which the liquid rises. The addition point for dissolved chlorine is always arranged downstream of the ethylene addition point. At least one addition point for liquid 1,2-dichloroethane follows each chlorine addition point, and the addition of the liquid 1,2-dichloroethane is carried out under kinetic energy which is high enough to enable a vigorous mixture of 1,2-dichloroethane, dissolved chlorine and ethylene to be carried out. Preferably, the liquid 1,2-dichloroethane is added by means of at least one jet mixer.

7 Claims, 2 Drawing Sheets

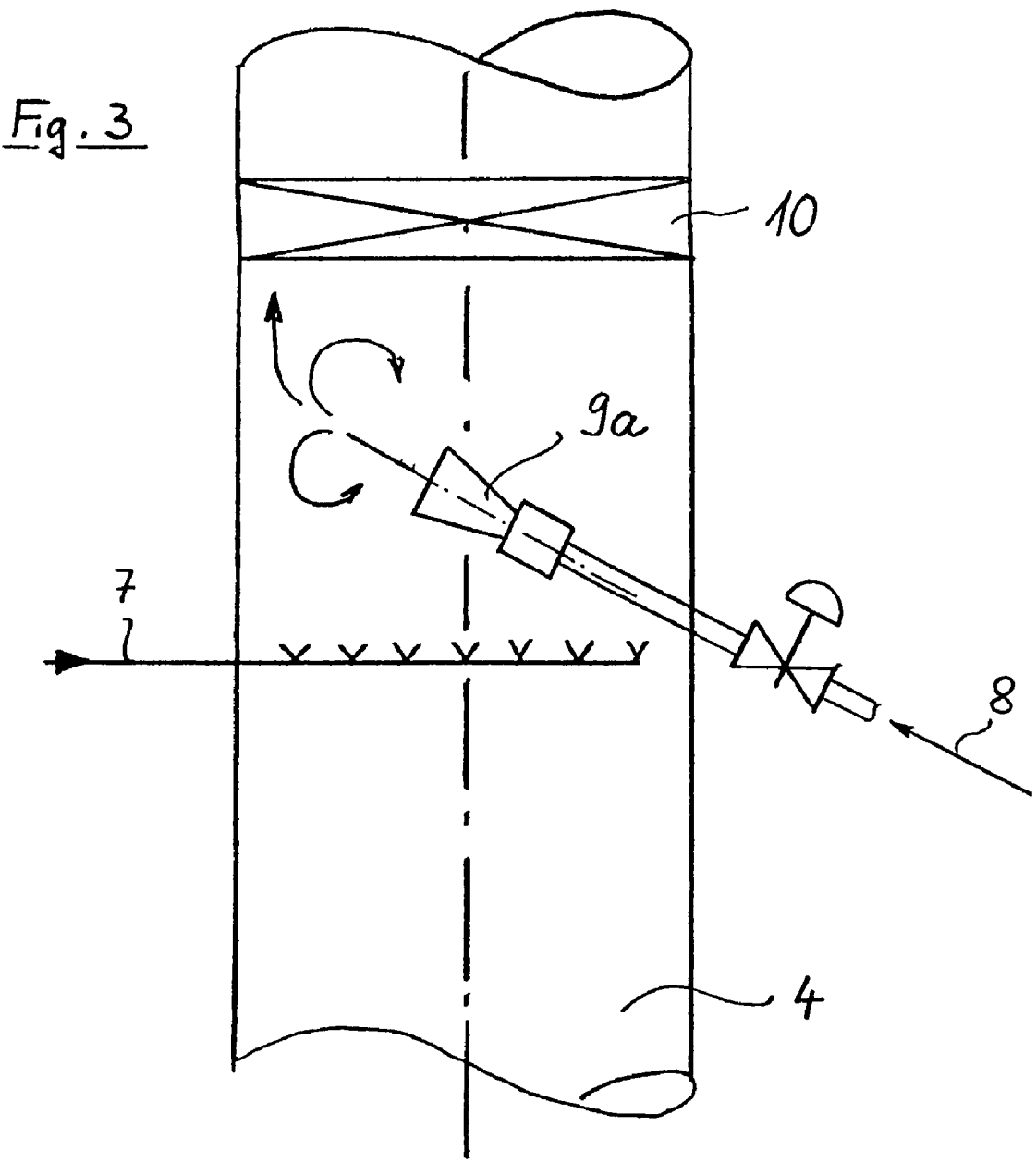

METHOD FOR PRODUCING 1,2-DICHLOROETHANE BY MEANS OF DIRECT CHLORINATION

BACKGROUND OF THE INVENTION

The invention relates to a process for the production of 1,2 dichloroethane, hereinafter referred to as EDC, which primarily serves as an intermediate product in the production of monomer vinyl chloride, hereinafter referred to as VCM, which, in turn, is used to produce polyvinyl chloride (PVC). When EDC reacts to form VCM, hydrogen chloride (HCl) is obtained. Hence, EDC is preferably produced from ethylene ($C_2H_4$) and chlorine ($Cl_2$) in a manner such as to maintain a balance between the hydrogen chloride (HCl) produced and consumed in the various reactions, as represented by the following reaction equations:

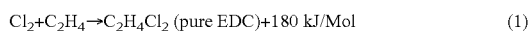

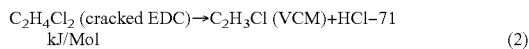

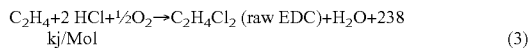

The process for the production of VCM with an adequate HCl balance —hereinafter referred to as "balanced VCM process"—comprises the following process steps:

direct chlorination in which one portion of the required EDC is produced from ethylene ($C_2H_4$) and chlorine ($Cl_2$) in the presence of a homogeneous catalyst and is made available as so-called pure EDC;

oxichlorination in which the remaining portion of the required EDC is produced from ethylene ($C_2H_4$), hydrogen chloride (HCl) and oxygen ($O_2$) and made available as so-called raw EDC;

fractionating EDC purification in which the raw EDC, together with the recycle EDC returned from the VCM fractionation step and, optionally, together with the pure EDC is freed from the secondary products formed in the oxichlorination and EDC pyrolysis steps in order to obtain a so-called feed EDC suitable for use in the EDC pyrolysis step; as an option, it is also possible to distil the pure EDC from the direct chlorination step in the heavy-ends column of the EDC distillation section;

EDC pyrolysis in which the feed EDC is thermally cracked, the mixture leaving the reactor, known as cracked gas, consists of VCM, hydrogen chloride (HCl) and non-reacted EDC as well as secondary products;

VCM fractionation in which the desired pure VCM product is separated from the cracked gas while the other essential substances, viz. hydrogen chloride (HCl) and non-reacted EDC contained in the cracked gas, are separately recovered as valuable materials and returned as recycle HCl or recycle EDC to the balanced VCM process.

In most industrial processes, a circulating stream of EDC reaction product is used as the reaction agent in direct chlorination. This can be accomplished in a loop-type reactor with external or internal circulation. The circulation can also be accomplished in a system with natural or forced circulation. In most cases ferric chloride is used as catalyst and in addition, sodium chloride which is able to inhibit the formation of heavy ends, may be admixed as an additive.

The state of the art as regards direct chlorination is, for instance, described in DE 199 10 964 A1. The process according to DE 199 10 964 A1 aims at suppressing side reactions, especially the continuation of the chlorination process of EDC to 1,1,2 trichloroethane, by making most of the chlorination reaction take place in the homogeneous liquid phase. The ethylene, which is less readily soluble in EDC than chlorine, is completely dissolved in the main stream of the circulating EDC reaction fluid in a co-current bubble column. The chlorine, which is more readily soluble in EDC than ethylene, is dissolved in a supercooled EDC part-stream and the resulting solution of chlorine in EDC is fed to the circulating main stream which already contains the dissolved ethylene.

Reaction (1), as a rule, is run with a slight ethylene surplus in order to avoid in any case any corrosion in the reaction system, the formation of secondary products at the end of the direct chlorination reaction and other problems associated with the treatment of chlorine-bearing outlet streams. Chlorine and ethylene are fed to the reactor by means of a ratio controller, the control variable being the ethylene content of the reaction outlet stream. In this case the aim is always to minimise the ethylene surplus at the reactor outlet to the extent possible in order to preclude too large an ethylene loss.

It was also found that reaction (1) produced a particularly high rate of secondary products when it was run as liquid phase reaction as shown in WO 03/070673 A1. This necessitates that ethylene is completely dissolved in the reaction tube prior to adding chlorine. The small gas bubbles generated by the gas distributor slowly grow by coalescence when travelling along this section and they finally reach a constant equilibrium size as a result of coalescence and decomposition activities. This impact adversely affects the mass transfer as the enlargement of the bubble diameter at a given total gas volume reduces the surface area available for mass transfer.

The kinetics of reaction (1) which takes place in the adjacent reaction zone in a largely homogeneous manner follows the velocity principle of the second order, hence at a very high velocity. The reaction velocity sharply drops at the end of the reaction zone when the ethylene and chlorine concentrations diminish gradually.

The overlapping effects that affect the ethylene solution behaviour, the reaction itself and the start of boiling clearly govern the sizing of a state-of-the-art boiling reactor and render a subsequent increase in capacity more difficult.

BRIEF SUMMARY OF THE INVENTION

The aim of the invention, therefore, is to provide an economical and efficient process that permits a high yield of product in as small a space as possible and hence an increase in capacity which does not require a larger external reactor diameter and which simultaneously supplies EDC of high purity.

DETAILED DESCRIPTION OF THE INVENTION

This task is realised in compliance with the technical details in claim 1. The said objective is solved as described below, the feed points for chlorine and dissolved ethylene being arranged in the leg of the loop in which the liquid can ascend, and any upstream feed point for ethylene being followed by a feed point for dissolved chlorine:

any feed point for chlorine is followed by at least one feed point for EDC, the addition of liquid EDC takes place with so much kinetic energy that a thorough mixture of EDC, dissolved chlorine and ethylene is effected.

Liquid EDC is normally available in most plants of this type because EDC, as a rule, is withdrawn from the reaction vessel and recycled for heat recovery. The EDC cooled slightly down is normally recycled to the leg section of the reaction vessel in which the downflow of liquid weakens. This permits the downflow of the liquid to be enhanced by an additional pulse reinforcing the natural circulation. It was now found that this additional pulse is not required if the yield by space is enlarged accordingly and consequently the total conversion of EDC, because the thermal effect thus obtained leads to an adequate enhancement of the natural circulation. In view of the fact that a gas/liquid phase interface continues to be absent within the zone of main reaction, which could catalyse the formation of secondary products, in particular 1,1,2 trichloroethane.

A further embodiment of the invention provides for the admixture of liquid 1,2 dichloroethane using one or several jet mixer/s which are also called tank mixers. The operating mode of such a mixer complies with a liquid jet pump. Typical applications of jet mixers are the mixture of the inventory of vessels or tanks for liquids in order to suppress any temperature or concentration gradient. The mixer is operated in a submerged position so as to make the kinetic energy of the jet draw the ambient medium and to mix the ambient vessel inventory to the propellant agent. The outlet stream of the jet mixer is the multiple of the propellant jet so that even large vessel inventories can be thoroughly mixed. The objective of the invention is to make use of jet mixers for exploiting the kinetic energy of the loop EDC so that the reaction partners chlorine and ethylene can be mixed as quickly as possible downstream of the feed point for dissolved chlorine.

Further embodiments of the invention relate to the arrangement of a jet mixer or of several jet mixers if applicable. The said mixer/s can be arranged within the loop reactor in such a manner that the liquid leaving them generates either a tangential stream as seen from the tube cross section and with the main stream flowing upwards, or an upward stream as seen from the longitudinal section and reinforcing the upward flow, or such that both flow directions are intensified. The jet mixer arrangement is located crosswise as seen from the longitudinal section or the tube cross section.

In the latter case, the outlet stream of the jet mixer/s flow/s in an upward oriented direction. When aligning the stream it is not detrimental to the flow if it contains a radial component, a criterion that will neither substantially affect the mixing ratio nor enhance it in any way. A specialist skilled in the art will opt for an upward direction of alignment when and if a static mixer is additionally mounted above the level of the jet mixers.

The measures described above reveal that a boiling reactor of conventional size can be revamped in accordance with the present invention so as to double the conversion rate according to reaction (1). The essential advantage of the invention, hence, consists in the unsophisticated revamping of the respective unit when increasing the capacity of existing plants. It is logical that this method becomes particularly efficient in the case of large-scale plants if the initial planning already includes the technicalities of the feed devices described in this invention.

The invention also encompasses the device required to run this process by means of a boiling reactor which consists of a degassing vessel, a reaction loop with natural circulation and withdrawal devices for EDC produced, and one or several jet mixers installed in at least one level and arranged in the manner described above. The said device may optionally be equipped with static mixers.

BRIEF DESCRIPTION OF THE DRAWINGS

The invention is illustrated on the basis of the example shown in FIG. 1 to FIG. 3.

FIG. 3 shows a longitudinal view of the ascending section of loop 4 in which the dissolution of ethylene has already taken place. In this case the dissolved chlorine 7 is metered and admixed via a plurality of nozzles arranged over the entire cross section. Jet mixer 9a fed with EDC 8 is mounted directly above the said chlorine metering section; the other jet mixers are not shown in the drawing but may be provided, and above mixer 9a there is static mixer 10. Jet mixer 9a is aligned upwards and enhances the stream contributing a pulse component which should compensate for the pressure loss caused by the static mixer, thus simultaneously producing as thorough a vortexing as possible.

Key to Reference Numbers

Figure 1:
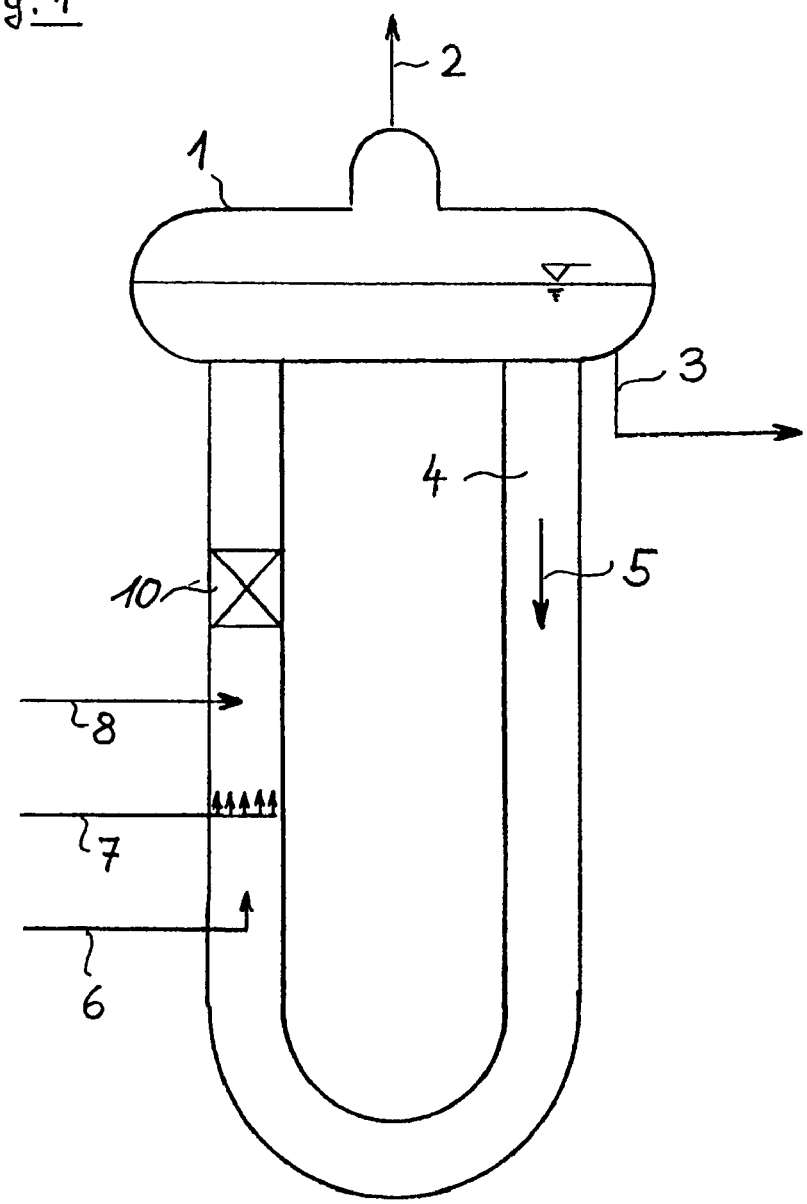
FIG. 1 shows a direct chlorination reactor that consists of degassing vessel 1, from which gaseous EDC 2 and liquid EDC 3 are withdrawn, and loop 4 circulating liquid EDC 5, which is represented by an arrow of direction and in which reaction (1) takes place. The ascending section of loop 4 houses successive feed points for ethylene 6, dissolved chlorine 7 and EDC 8; however, a plurality of feed points may also be arranged in the loop reactor itself.
Figure 2:
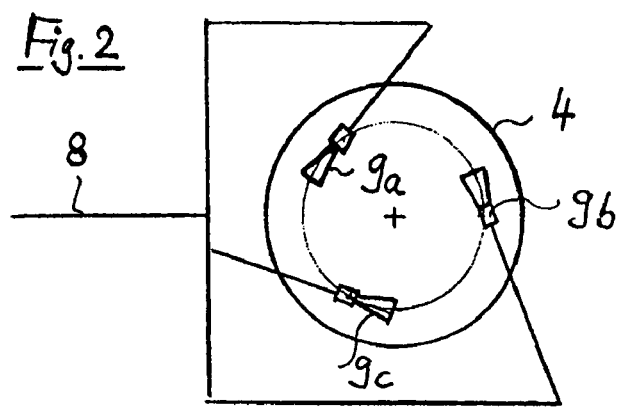
FIG. 2 is a cross-sectional view of the ascending tubular section of loop 4, with the arrangement of three jet mixers 9a, 9b and 9c referred to in this example and fed with EDC 8. The EDC used for this purpose may form either from the withdrawn liquid EDC 3 upon release of heat or from condensed EDC 2 that was gaseous before and is returned. It is of course possible to exploit a mixture of both. In accordance with FIG. 1, a static mixer may be mounted above the level of the jet mixers.

1 Degassing vessel
2 Gaseous EDC
3 Liquid EDC
4 Loop
5 Liquid EDC
6 Feed point for ethylene
7 Feed point for chlorine
8 EDC
9a Jet mixer
9b Jet mixer
9c Jet mixer
10 Static mixer

The invention claimed is:

1. A process for the production of 1,2-dichloroethane of high purity from dissolved chlorine and dissolved ethylene that come into contact with each other in the presence of a circulated liquid reaction agent, the agent primarily consisting essentially of 1,2-dichloroethane and a catalyst, using at least one reaction unit arranged vertically and designed as loop, the two leg sections of the loop communicating with a degassing vessel arranged above the unit, the degassing vessel serving for the withdrawal of the reaction product in gaseous or liquid form or in both forms, the feed points for chlorine and dissolved ethylene being located in the loop leg section in which the liquid ascends, any upstream feed point for ethylene being followed by a downstream feed point for dissolved chlorine, wherein any feed point for chlorine is followed by at least one feed point for liquid 1,2-dichloroethane, and the addition of liquid 1,2-dichloroethane takes place with so much kinetic energy that a thorough mixture of 1,2-dichloroethane, dissolved chlorine and ethylene is effected.

2. The process according to claim 1, wherein the addition of liquid 1,2-dichloroethane is effected by means of at least one jet mixer.

3. The process according to claim 2, wherein the at least one jet mixer is arranged in the loop reactor in such a manner that the liquid leaving the mixers flows crosswise to the upward main stream direction.

4. The process according to claim 2, wherein the at least one jet mixer is arranged in the loop reactor in such a manner that the liquid leaving the mixers generates a tangential stream as seen from tube cross section, the said stream overlapping and extending over the upward main stream direction.

5. The process according to claim 2, wherein the at least one jet mixer is arranged in the loop reactor in such a manner that the liquid leaving the mixer generates an upward stream as seen from the longitudinal section, the said stream reinforcing the upward main stream direction.

6. The process according to claim 2, wherein the at least one jet mixer is arranged in the loop reactor in such a manner that the liquid leaving the mixer generates an upward stream as seen from the longitudinal section, the said stream reinforcing the upward main stream direction.

7. The process according to claim 2, wherein a static mixer is added to the jet mixers, the static mixer being arranged in the upward loop section of the loop reactor.

* * * * *